United States Patent
Barbouche et al.

(10) Patent No.: US 10,169,537 B2
(45) Date of Patent: *Jan. 1, 2019

(54) SYSTEM AND METHOD FOR THE VISUALIZATION OF MEDICAL DATA

(71) Applicant: Forward Health Group, Inc., Madison, WI (US)

(72) Inventors: Michael Barbouche, Madison, WI (US); Joel May, Madison, WI (US); John Studebaker, Tulsa, OK (US); Sean Thomas, Middleton, WI (US); Joel Walker, Cedarburg, WI (US)

(73) Assignee: Forward Health Group, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,405

(22) Filed: Jun. 9, 2017

(65) Prior Publication Data
US 2017/0372008 A1 Dec. 28, 2017

Related U.S. Application Data (63) Continuation of application No. 13/908,413, filed on Jun. 3, 2013, now Pat. No. 9,679,105.

(60) Provisional application No. 61/656,338, filed on Jun. 6, 2012.

(51) Int. Cl.
*G06F 19/00* (2018.01)
*G16H 50/70* (2018.01)

(52) U.S. Cl.
CPC ............ *G06F 19/321* (2013.01); *G06F 19/00* (2013.01); *G16H 50/70* (2018.01); *G06F 19/328* (2013.01)

(58) Field of Classification Search
CPC ... G06F 19/321; G06F 19/3443; G06F 19/328
See application file for complete search history.

(56) References Cited

U.S. PATENT DOCUMENTS

| | | | |
|---|---|---|---|
| 6,188,403 B1* | 2/2001 | Sacerdoti | G06F 17/30554 345/440 |
| 6,202,060 B1 | 3/2001 | Tran | |
| 6,440,066 B1 | 8/2002 | Bardy | |
| 6,587,855 B1 | 7/2003 | Ellmann et al. | |
| 7,376,680 B1* | 5/2008 | Kettler | G06F 17/30303 |
| 7,523,042 B2 | 4/2009 | Hunt et al. | |
| 8,092,382 B2 | 1/2012 | Bardy | |
| 9,679,105 B2 | 6/2017 | Barbouche et al. | |
| 2003/0074222 A1 | 4/2003 | Rosow et al. | |
| 2006/0112110 A1* | 5/2006 | Maymir-Ducharme | G06F 17/30616 |

(Continued)

OTHER PUBLICATIONS

2011 Physician Quality Reporting System (Physician Quality Reporting) Measure Specifications Manual for Claims and Registry Reporting of Individual Measures, Version 5.3, Copyright 2010, American Medical Association, 571 pages.

(Continued)

*Primary Examiner* — William A Beutel
(74) *Attorney, Agent, or Firm* — Patterson Thuente Pedersen, P.A.

(57) ABSTRACT

The systems and methods of the present application includes embodiments that allow users to more easily and efficiently compare medical data in an automated, computerized system using a variety of visualization tools, by operation on datasets sourced from a variety of entities.

20 Claims, 8 Drawing Sheets

(56) References Cited

U.S. PATENT DOCUMENTS

| | | |
|---|---|---|
| 2009/0112882 A1 | 4/2009 | Maresh et al. |
| 2009/0217189 A1* | 8/2009 | Martin ............... G06F 19/3406 715/772 |
| 2009/0259488 A1 | 10/2009 | Gounares et al. |
| 2009/0319523 A1 | 12/2009 | Anderson et al. |
| 2010/0332453 A1* | 12/2010 | Prahlad ............... G06F 11/1458 707/640 |
| 2011/0099500 A1 | 4/2011 | Smith et al. |
| 2011/0153384 A1 | 6/2011 | Horne et al. |
| 2011/0191284 A1 | 8/2011 | Dalton |
| 2011/0238488 A1* | 9/2011 | Hahn ................ G06F 17/30528 705/14.42 |
| 2012/0116985 A1 | 5/2012 | Rastogi |
| 2012/0221553 A1* | 8/2012 | Wittmer ............ G06F 17/30572 707/722 |
| 2014/0022255 A1 | 1/2014 | Barbouche et al. |

OTHER PUBLICATIONS

The National Academies Press, Pathways to Quality Health Care: Performance Measurement—Accelerating Improvement, Institute of Medicine of the National Academies, Copyright 2006, 383 pages.
Application and File History for U.S. Appl. No. 13/908,413, filed Jun. 3, 2013, Inventor: Barbouche et al.

* cited by examiner

SYSTEM AND METHOD FOR THE VISUALIZATION OF MEDICAL DATA

RELATED APPLICATION

This application is a continuation of U.S. application Ser. No. 13/908,413 filed Jun. 3, 2013, now U.S. Pat. No. 9,679,105 issued Jun. 13, 2017, which claims the benefit of U.S. Provisional Application No. 61/656,338 filed Jun. 6, 2012, each of which is hereby fully incorporated herein by reference.

FIELD OF THE INVENTION

The invention relates generally to data processing, and more particularly, to methods and systems for the automated visualization of patient medical information and data.

BACKGROUND OF THE INVENTION

With recent advances in electronic medical records (EMRs) and the widespread adoption of electronically-recorded medical data, there exist vast repositories of information related to the medical industry. However, these data are often sourced from many different entities. For example, medical practitioners, payors, insurance carriers, hospitals, clinics, laboratories, governmental organizations, and charitable organizations, among others, may record, store, or otherwise manage some aspect of data related to diseases, diagnoses, treatments, outcomes, symptoms, prognoses, or clinical studies, or even result-based data of individual physicians or hospitals.

Electronic medical records, for example, are typically prepared and managed by the creator of the record, generally a health care practice or facility. Diagnostic laboratories may prepare and manage data related to individual clinical specimens in order to determine information about the health of a patient. These data are often stored in a database separate from or in addition to the EMR record. Additionally, healthcare payors may prepare and manage data related to the financial side of the healthcare of a patient or the efficiency of effectiveness of the treating practitioner. Clearly, each sourcing entity has different objectives and motivations. There is thus very little continuity between the datasets of the above-described entities, despite the fact that the data may all be related to healthcare, and even the health care of the same patient.

In addition to a lack of continuity in dataset formats and sources from medical providers and payors, patients also contribute to the challenges of managing and present information about medical data and records. Patients may see different providers and obtain different diagnostics tests without the providers being aware that second opinions have been sought by the patient. Datasets across all of the providers and payors for a given patient can thus show conflicting information, even for the same patient in ostensibly the same circumstances.

As the healthcare industry shifts in the way medical practitioners are affiliated, medical practitioners are moving from independent, self-employed entities to employees of a particular clinic or hospital. Analysts expect that the recently enacted Patient Protection and Affordable Care Act (PPACA), which reforms certain aspects of the private health insurance industry and public health insurance programs, will further propagate this shift. Accordingly, there may be more opportunities for practice groups in a given provider or organization to want to compare practice results and patient outcomes across the group or organization.

It would be desirable to provide for better tools and techniques for improving the ability to easily and efficiently compare medical data in an automated, computerized system using a variety of visualization tools that can accommodate medical data sourced from various entities.

SUMMARY OF THE INVENTION

The systems and methods of the present application includes embodiments that allow users to more easily and efficiently compare medical data in an automated, computerized system using a variety of visualization tools, by operation on datasets sourced from a variety of entities.

Embodiments allow users to easily and efficiently compare medical data using a variety of visualization tools, by operation on datasets sourced from a variety of entities. In an embodiment, a system comprises a database, an application layer, and a dashboard. The database is populated by normalized data from one or more datasets. The application layer comprises the intermediate layer enabling communication between the database and the dashboard. In embodiments, the dashboard is configured to display medical data in Venn diagram-type output, a scatter plot-type output, and/or an orbit plot-type output.

In one embodiment, a dashboard is configured to display Venn diagram-type output of data retrieved across a plurality of datasets for relevant patient populations of a given practice group within a medical provider or within an entire medical provider or payor organization. In this embodiment, the respective data is retrieved across datasets, normalized by the system, and after denominators using specific definitions are calculated to describe specific populations, the union and non-union of a population can then be displayed with respect to other populations. In a simple graphical view, a user can readily understand the relative relation between two or more given populations—those elements or members of the population that overlap and thus have similarities with another population, and those elements or members that do not overlap and thus do not have similarities with another population. The metadata that describes the patient population, or denominator, is therefore what the Venn diagram output displays. For example, for a particular medical practitioner, the number of patients that have been diagnosed with coronary artery disease, diabetes, and hypertension, respectively, can be output in a Venn diagram to illustrate not only medical trends or relationships among the respective diseases, but also trends or relationships for that particular medical practitioner. In embodiments, the grouping aspect elicits information from the intersection of patient and provider data to identify outliers from the combination of this data. In embodiments, the Venn diagram-type output is interactive such that details of particular data sections can be retrieved by user manipulation, such as by clicking, dragging, or hovering over the desired union or non-union section. In embodiments, once a particular section is selected, the dashboard displays the patients and/or the details of the patients in the chosen section.

In another embodiment, a dashboard is configured to display a scatter plot-type output of data retrieved across a plurality of datasets for relevant patient populations of a given practice group within a medical provider or within an entire medical provider or payor organization. In this embodiment, once the respective data is retrieved across datasets and normalized by the system, the user can select two sets of categorical characteristics and two sets of continuous characteristics, via the dashboard, to be shown for each patient. In other embodiments, other quantities of categorical characteristics or continuous characteristics are utilized. In embodiments, a letter, symbol, shape, or color can be utilized to express the categorical characteristics. In other embodiments, a simple point is utilized. Continuous data is positioned along the X and Y axes to illustrate the relative position of the marker. For an entire dataset, patterns or trends are then readily viewed. For example, a scatter plot-type output can be displayed for all patients belonging to a payor or set of payors for a particular type of medical test. In embodiments, the scatter plot-type output is interactive such that details of particular data points can be retrieved by user manipulation, such as by clicking, dragging, or hovering over the desired data point.

In another embodiment, a dashboard is configured to display an orbit plot-type output of data retrieved across a plurality of datasets for relevant patient populations of a given practice group within a medical provider or within an entire medical provider or payor organization. In this embodiment, once the respective data is retrieved across datasets and normalized by the system, the user can select a timeframe to view patient data. In an embodiment, two sliders, a left slider controlling the bound of the earliest date, and a right slider controlling the bound of the latest date, define the timeframe. In embodiments, the patient embodies an originating orbit or circle. Healthcare events extend from the patient orbit in their own orbits, with other healthcare events extending from the original events. Each orbit can further comprise descriptive event information or numerical representations. Relationships between events can then be readily viewed. In embodiments, the size of the orbit is defined by the time, severity, or cost, of the event, for example. Different colors and shapes of orbits can be used, in embodiments, to express other information to the user, for example, the identity of the entity, the size of the entity, or the cost of the event.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention, in connection with the accompanying drawings, in which.

While the invention is amenable to various modifications and alternative forms, specifics thereof have by shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

Aspects of the invention are captured within the software code, a copy of which is submitted herewith in Appendices A-H and incorporated by reference herein.

Figure 1:
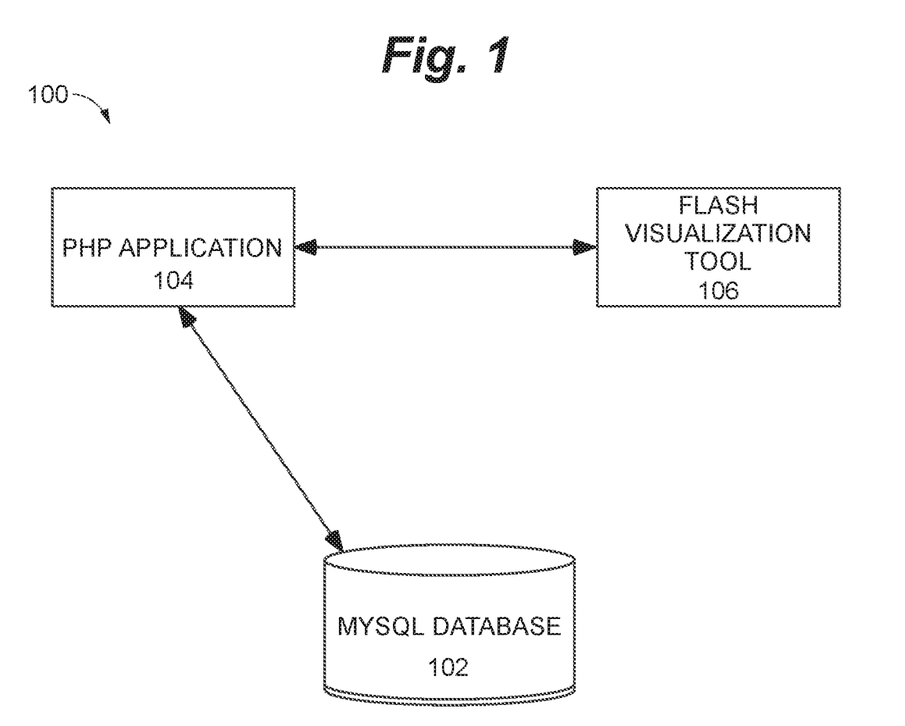
FIG. 1 is a block diagram of a visualization system, according to an embodiment.

Referring to FIG. 1, a visualization system 100 is depicted, according to an embodiment. Visualization system 100 generally includes a database 102, application layer 104, and dashboard 106. While visualization system 100 is described herein with respect to a cloud-based system, embodiments of the invention can be performed in a cloud computing, client-server, or standalone computer processing environment, or any combination thereof. To that end, any of the components of system 100 can be located in a singular "cloud" or network, or spread among many clouds or networks. In another embodiment, system 100 can comprise a single computer or server having a processor and memory, whereby the processor is configured to carry out the instructions of a computer program, which is stored in memory. End-user knowledge of the physical location and configuration of components of system 100 is not required.

Figure 2:
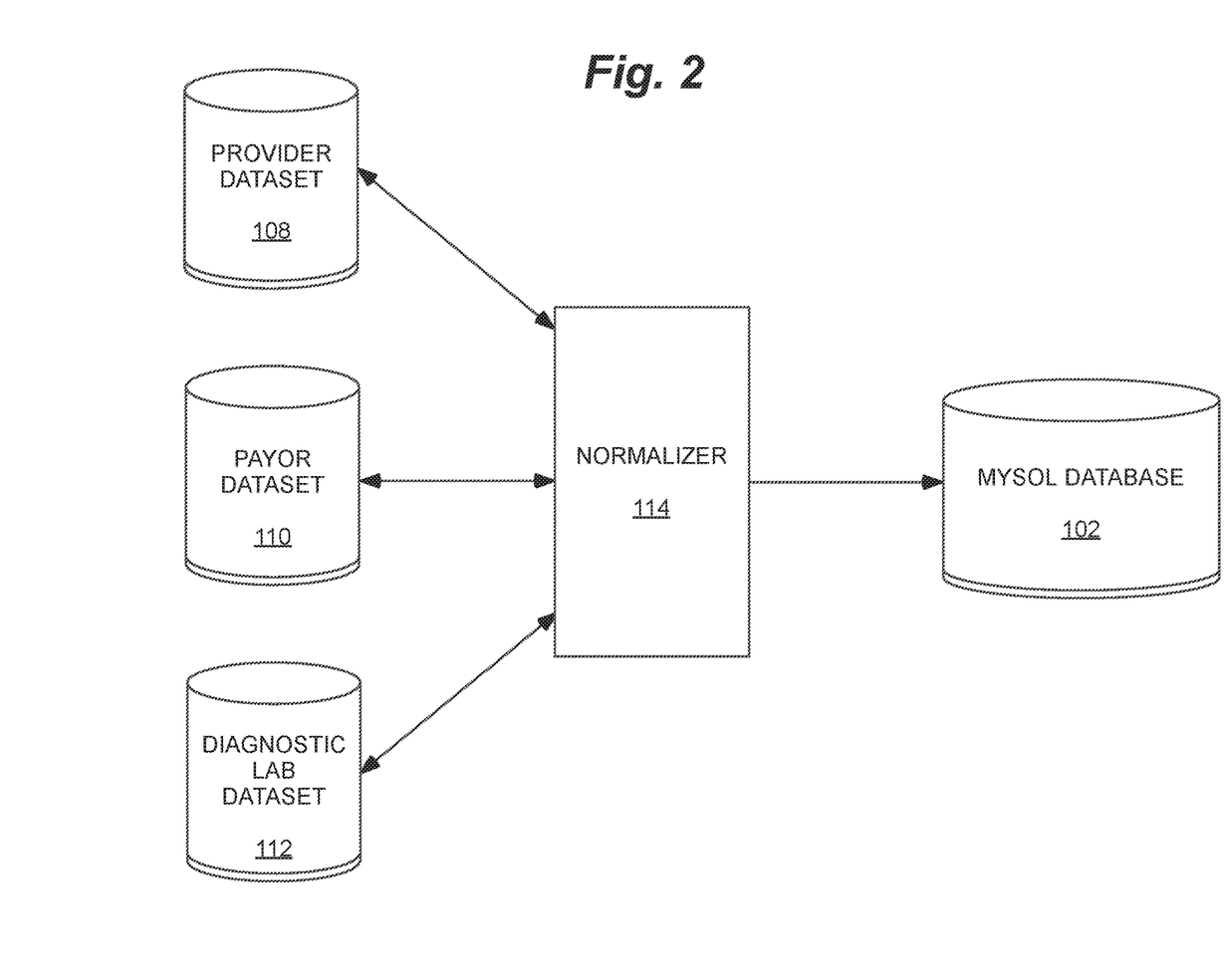
FIG. 2 is a block diagram of back-end components of a visualization system, according to an embodiment.

Referring to FIGS. 1 and 2, database 102 is depicted as a SQL database, although database 102 can also comprise data storage as implemented by general purpose database management storage systems (DBMS) as implemented by, for example, Oracle, IBM DB2, Microsoft SQL Server, PostgreSQL, My SQL, or SQLite solutions. In other embodiments, database 102 can comprise a flat file or series of files. In embodiments, database 102 can comprise simple non-volatile memory as part of a computer. In other embodiments, database 102 can comprise a relational database or series of databases. The foregoing lists in no way limit the type of database or structure of database that can be used, as these embodiments are given only by way of example and are not intended to limit the scope of the invention.

Database 102 is populated by the normalization of one or more datasets. For example, referring to FIG. 2, provider dataset 108, payor dataset 110, and diagnostic lab dataset 112 all comprise the respective medical data stored by the respective managing entities (provider, payor, and diagnostic lab) as desired by the respective entities. Provider dataset 108 can comprise, for example, EMR data. Payor dataset 110 can comprise, for example, financial records or efficiency data. Diagnostic lab dataset 112 can comprise clinical specimen or testing data. Each of these datasets can be stored discretely on a separate database as implemented by any of the database embodiments listed above with respect to database 102.

Normalizer 114 can execute database-specific calls to retrieve data from provider dataset 108, payor dataset 110, and/or diagnostic lab dataset 112. The data retrieved from the respective datasets is analyzed by normalizer 114 and organized to minimize redundancy and dependency. Normalizer 114 can then execute database-specific calls to database 102 to store the normalized data into database 102. For example, basic patient information that is redundant between the datasets, such as demographic data, etc., can be consolidated. Likewise, data common to each particular patient can be correlated among datasets to create a data superset for each patient. Additional or fewer datasets or different datasets can be incorporated by normalizer 114 into database 102 in other embodiments. In embodiments, for example, provider dataset 108 can comprise the data for provider dataset 108 and diagnostic lab dataset 112.

In an embodiment, normalizer 114 is also configured to create a set of metadata pertaining to at least one quality measure of the data. A denominator can be calculated with specific definitions to describe the data. The denominator therefore describes the patient population based on the at least one quality measure of the data. In embodiments, the denominator describes the patient data based on two or more quality measures. In embodiments, the calculation of a denominator facilitates the display of data through dashboard 106.

Referring again to FIG. 1, application layer 104 is depicted as a PHP Application, although implementation using any programming language or combinations of languages is captured by embodiments of system 100. In an embodiment, application layer 104 comprises the intermediate layer enabling communication between database 102 and dashboard 106. Application layer 104 is configured to execute database-specific calls to retrieve and store data in database 102. Likewise, application layer 104 is configured to receive data and transmit data to dashboard 106 for display to a user. In essence, application layer 104 enables set-up and data routing services for a user accessing dashboard 106 utilizing data from database 102.

Dashboard 106 is depicted in FIG. 1 as a Flash Visualization Tool, although implementation using any programming language or combinations of languages is captured by embodiments of system 100. In an embodiment, dashboard 106 comprises the set of visualization tools for a user viewing the data of database 102 in graphical or other form. Thus, dashboard tool 106 can comprise any number of different views or displays. In embodiments, dashboard 106 comprises a Venn-diagram-type view, a scatter plot-type view, and/or an orbit plot-type view.

Figure 3:
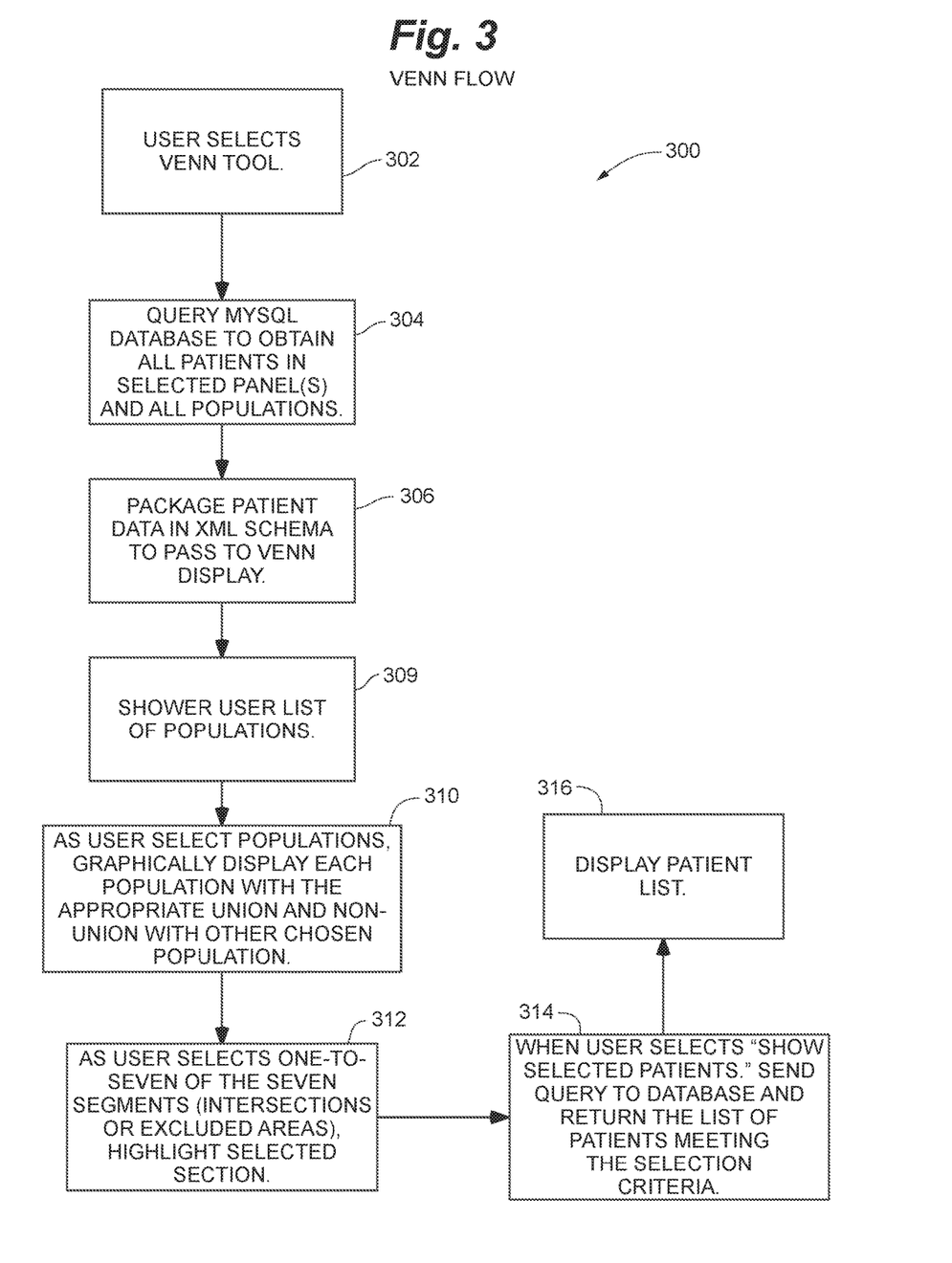
FIG. 3 is a flowchart of a method of visualizing medical data using a Venn diagram, according to an embodiment.
Figure 4:
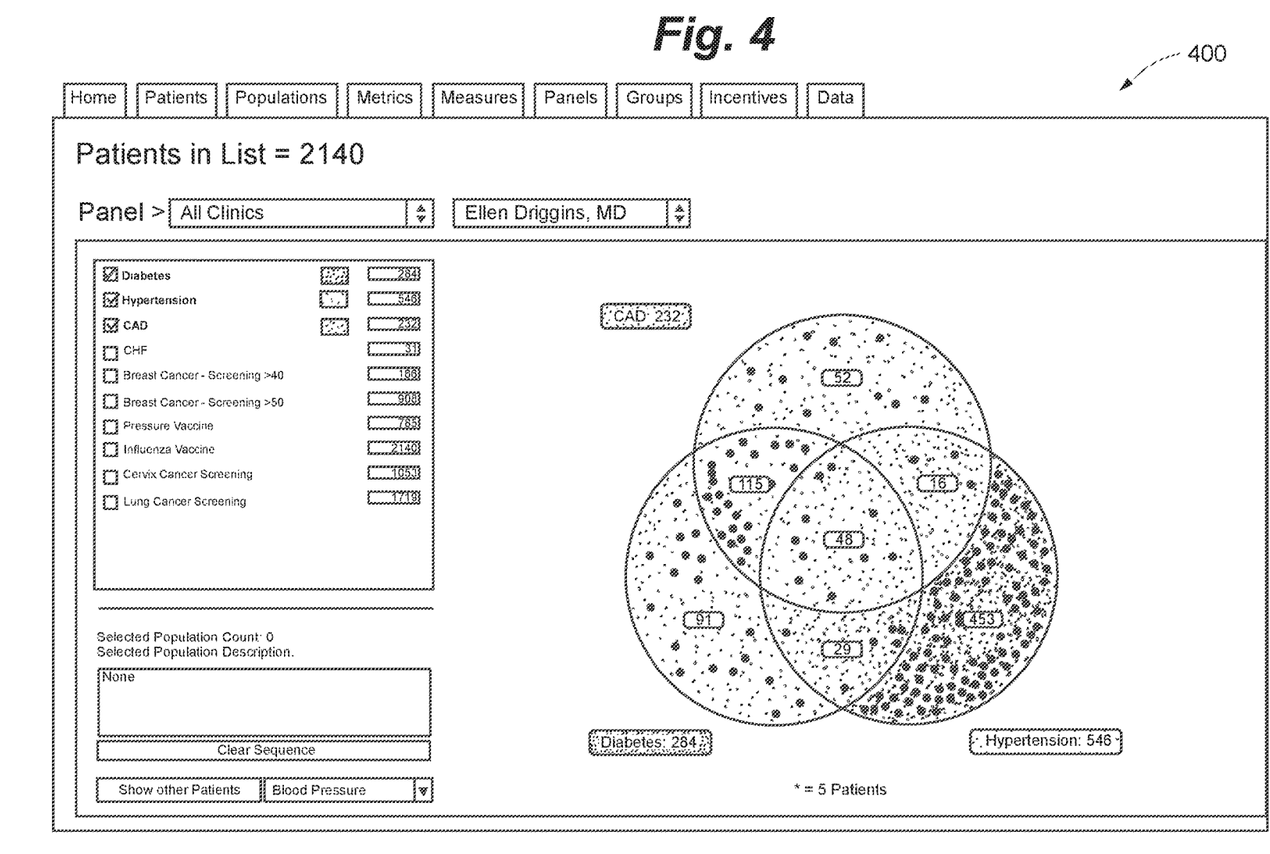
FIG. 4 depicts a dashboard display of a Venn diagram created by the method depicted in FIG. 3, according to an embodiment.

Referring to FIG. 3, a method of visualizing medical data using a Venn diagram 300 via dashboard 106 is illustrated, according to an embodiment. At 302, a user selects the Venn diagram tool via dashboard 106. At 304, application layer 104 queries database 102 to obtain all patients in the selected panel or panels and all populations. At 306, the data is retrieved from database 102 by application layer 104 and packaged in a patient data XML, schema to pass to dashboard 106. At 308, dashboard 106 unpacks the data and a user list of populations is shown to the user. At 310, as the user selects populations, dashboard 106 graphically displays each population with the appropriate union and non-union, as compared to the other chosen populations. At 312, as the user selects a number of segments, as intersections or excluded areas, and those areas are highlighted by dashboard 106. As depicted in FIG. 3, the number of segments, in an embodiment, can be from one to seven. In other embodiments, the number of segments can be greater or less than seven. For example, one circle has one segment. Two circles have three segments, although the union segment could be empty (no patients in the segment). Three circles have seven segments, again although any one of the segments could be empty (no patients in the segment). At 314, a user can select an option to "show selected patients" based on the chosen number of segments. Database 102 is then queried, via application layer 104, and the list of patients meeting the selection criteria is returned. These data are packaged by application layer 104 and passed to dashboard 106. At 316, the patient data meeting the selection criteria is unpacked and displayed by dashboard 106. The resulting Venn diagram view 400 of dashboard 106 is illustrated in FIG. 4.

Figure 5:
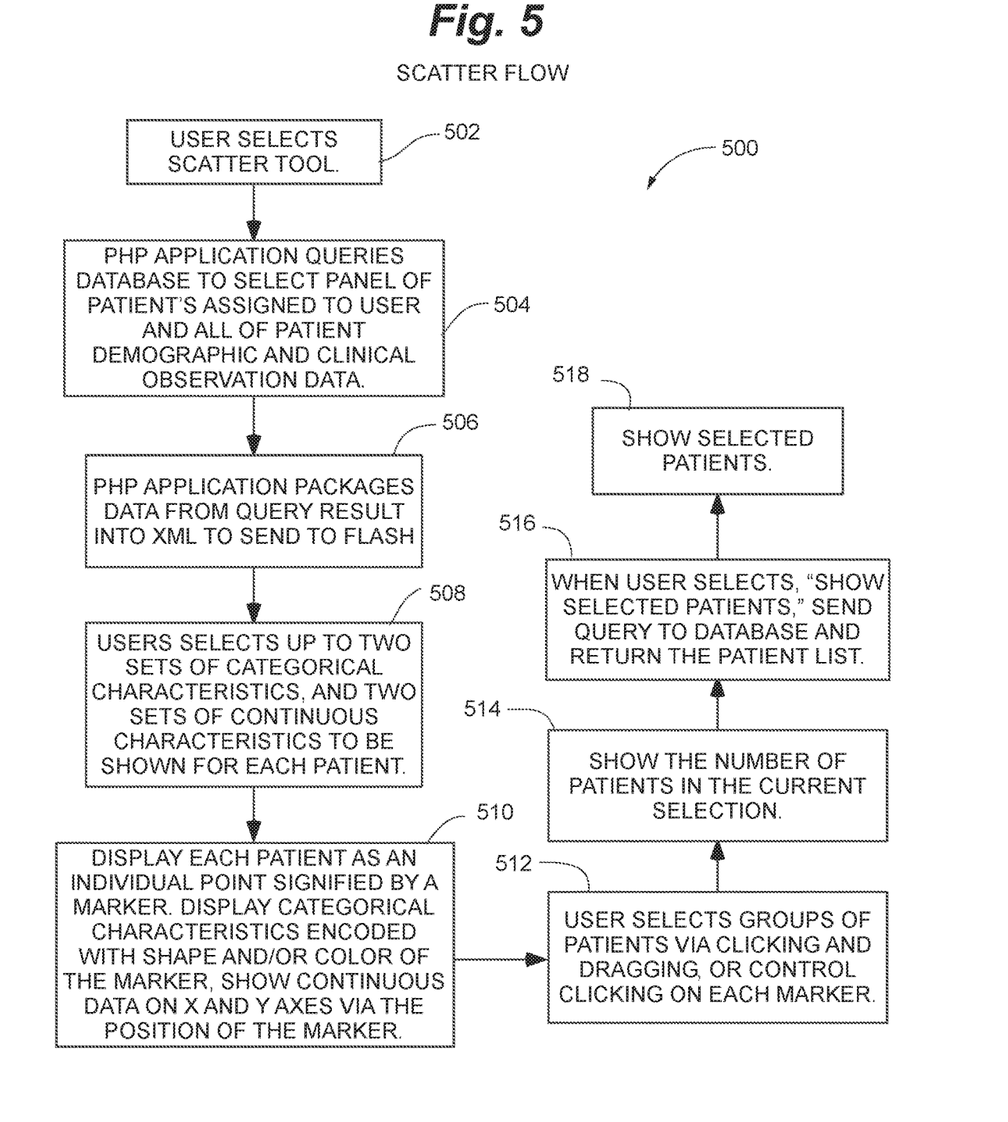
FIG. 5 is a flowchart of a method of visualizing medical data using a scatter plot, according to an embodiment.
Figure 6:
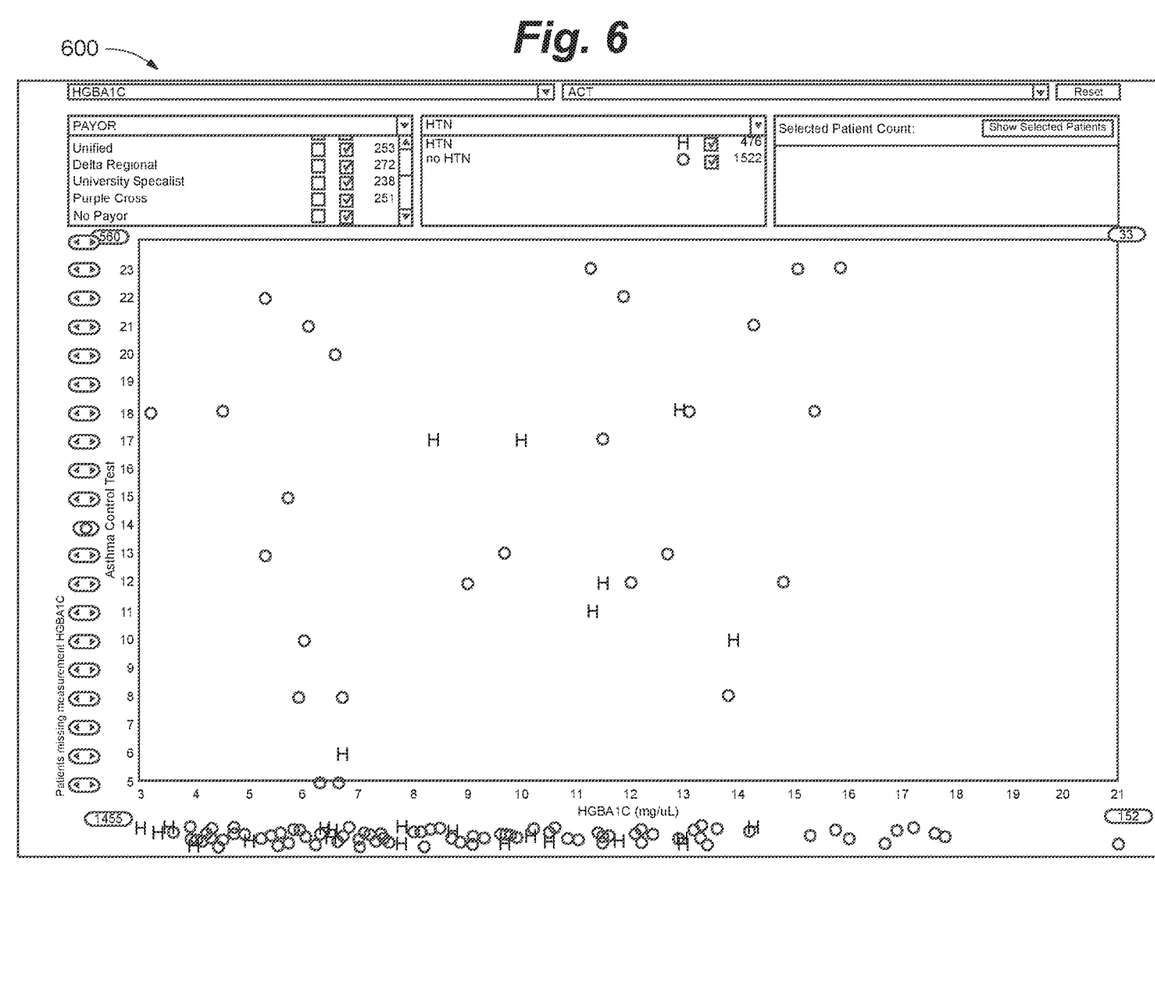
FIG. 6 depicts a dashboard display of a scatter plot created by the method depicted in FIG. 5, according to an embodiment.

Referring to FIG. 5, a method of visualizing medical data using a scatter plot diagram 500 via dashboard 106 is illustrated, according to an embodiment. At 502, a user selects the scatter plot tool via dashboard 106. At 504, application layer 104 queries database 102 to select a panel of patients assigned to the user and all of the patient demographic and clinical observation data. In embodiments, users can also query data on patients not assigned to them, depending on the particular role of the user. At 506, the data is retrieved from database 102 by application layer 104 and packaged in a patient data XML, schema to pass to dashboard 106. At 508, dashboard 106 unpacks the data, and the user can select up to two sets of categorical characteristics and two sets of continuous characteristics to be shown for each patient. In other embodiments, other quantities of categorical characteristics or continuous characteristics are utilized. At 510, a data point representing each patient is displayed by a marker. In embodiments, a letter, symbol, shape, or color can be utilized to express the categorical characteristics. In other embodiments, a simple point is utilized. Further, continuous data is positioned along the X and Y axes of dashboard 106 to illustrate the relative position of the marker. At 512, the user can select groups of patients via clicking or dragging, control-clicking, or any other suitable user input on each marker. At 514, dashboard 106 displays the number of patients in the current selection. At 516, the user can select an option to "show selected patients" based on the current user input for groups of patients selection. Database 102 is then queried, via application layer 104, and the list of patients meeting the selection criteria is returned. These data are packaged by application layer 104 and passed to dashboard 106. At 518, the patient data meeting the selection criteria is unpacked and displayed by dashboard 106. The resulting scatter plot diagram view 600 of dashboard 106 is illustrated in FIG. 6.

Figure 7:
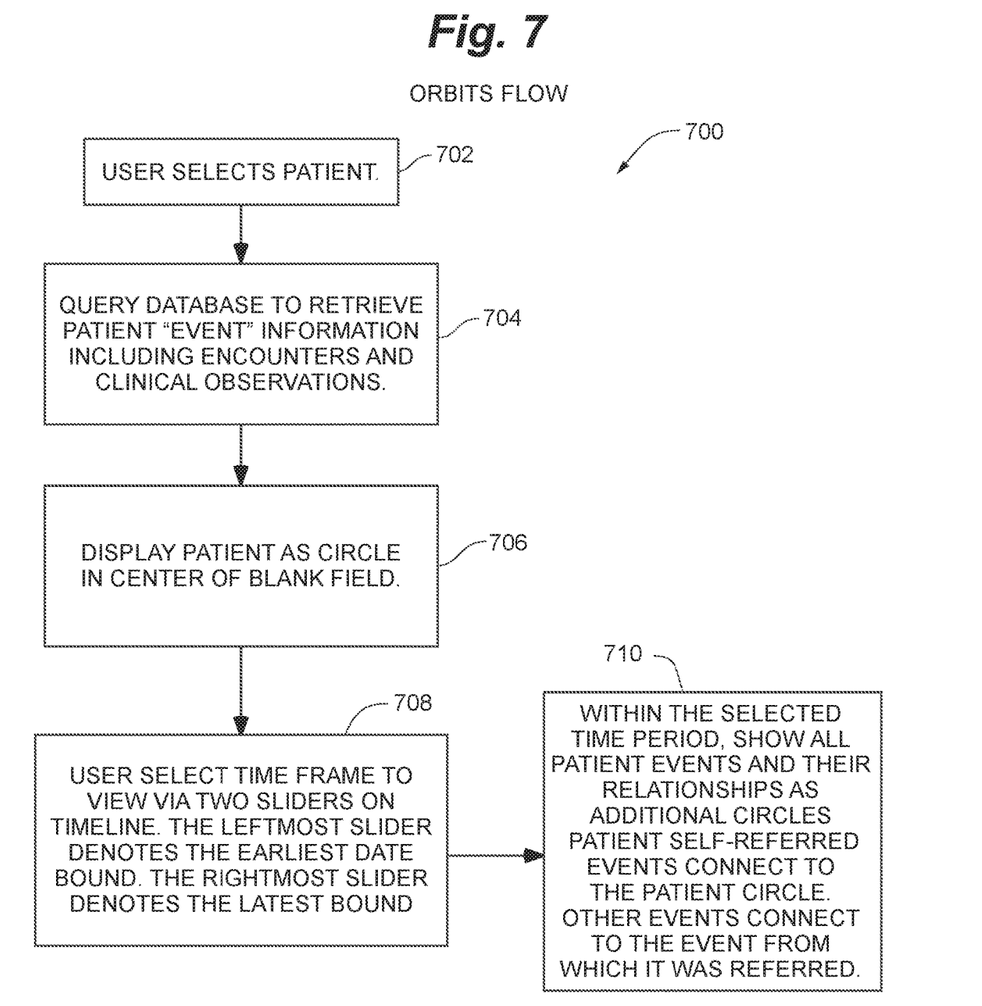
FIG. 7 is a flowchart of a method of visualizing medical data using an orbit plot, according to an embodiment.
Figure 8:
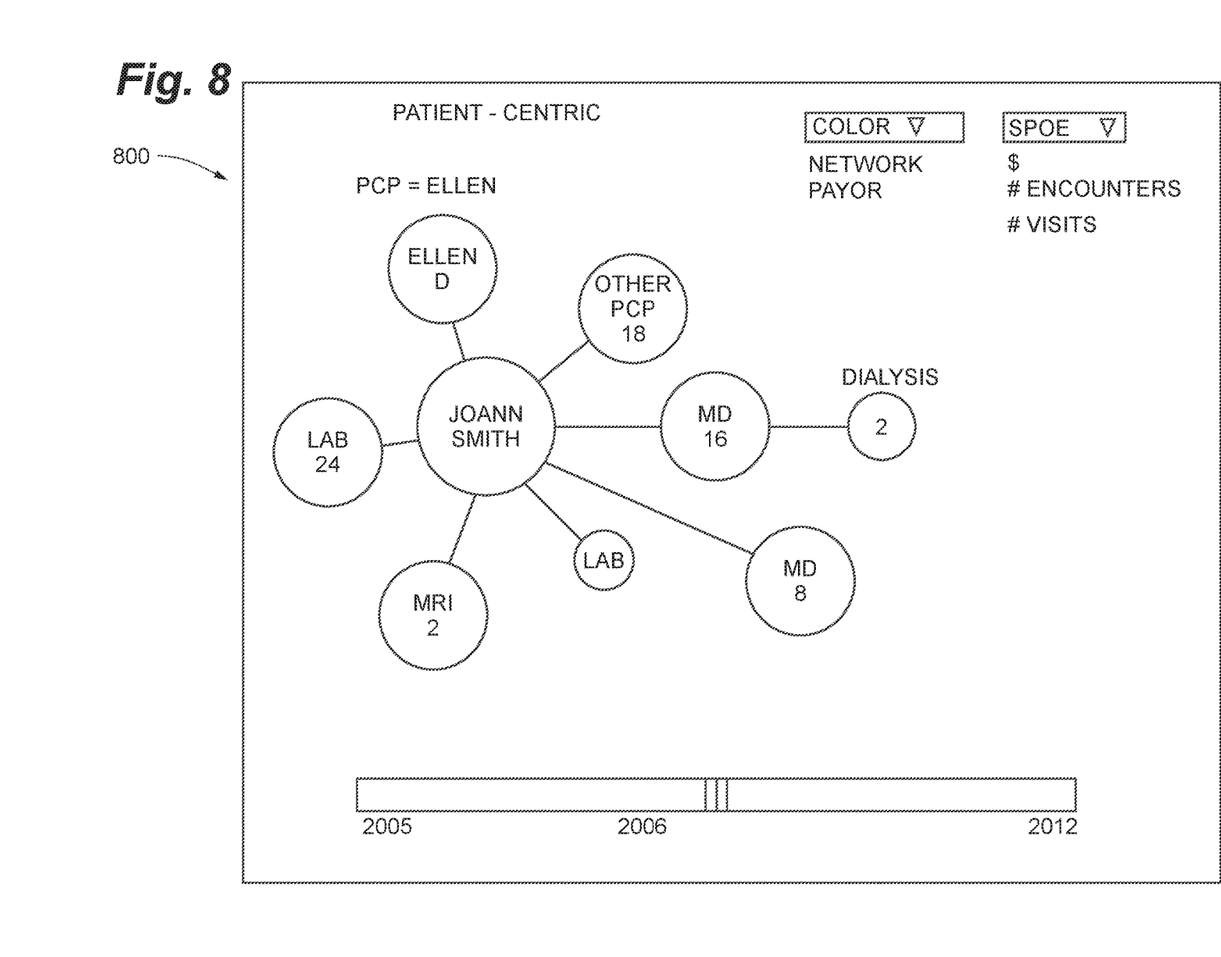
FIG. 8 depicts a dashboard display of an orbit plot created by the method depicted in FIG. 6, according to an embodiment.

Referring to FIG. 7, a method of visualizing medical data using an orbits plot diagram 700 via dashboard 106 is illustrated, according to an embodiment. At 702, a user selects a particular patient via dashboard 106. At 704, application layer 104 queries database 102 to retrieve patient "event" information including encounters and clinical observations and subsequently packages the data in a patient data XML schema to pass to dashboard 106. At 706, dashboard 106 unpacks the data and the selected patient is displayed as a circle or orbit in the center of an otherwise blank field. At 708, the user can select a timeframe to view via two slider bars. In embodiments, the year or other suitable time delineation is displayed proximate to the slider bar. In other embodiments, the timeframe selection can be by any other suitable graphical user interface. At 710, the user selection is evaluated such that patient events meeting the selected criteria are displayed as additional circles or orbits. Further, the relationship between events is likewise displayed by connection of related events. In an embodiment, patient self-referred events connect to the patient circle or orbit. Other events connect to the event from which the event was referred. Each orbit can further comprise descriptive event information or numerical representations. In embodiments, the size of the orbit is defined by the time, severity, or cost, of the event, for example. Different colors and shapes of orbits can be used, in embodiments, to express other information to the user, for example, the identity of the entity, the size of the entity, or the cost of the encounter. The resulting orbits plot diagram view 800 of dashboard 106 is illustrated in FIG. 8.

Various embodiments of systems, devices, and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

What is claimed is:

1. A computer-implemented method for the automated visualization of patient medical information and medical data over an Internet network, comprising:
    storing medical data of patients for each of at least one medical provider and at least one payor organization in a plurality of datasets, wherein each of the datasets in the plurality of datasets is stored in a computer memory accessible over the Internet network separately from each of the other datasets, each of the plurality of datasets including at least an electronic medical record and a secondary healthcare record, the electronic medical record and the secondary healthcare record stored separately and having at least one common key;
    normalizing the medical data by executing database-specific calls to each of the datasets over the Internet network and retrieving at least some of the medical data from the plurality of datasets by a normalizer, the normalizer configured to generate a set of metadata based on at least one quality measure of the medical data and generate normalized medical data for the set of metadata using a denominator to define a patient population having the at least one quality measure;
    populating a database with the normalized medical data, the database operably coupled to the Internet network, wherein the normalized medical data is stored separately from the plurality of datasets to create a medical data superset for each patient including medical data common to each patient stored among the plurality of datasets;
    configuring an application layer operably coupled to the Internet network to enable communication between the database of the medical data superset for each patient and a dashboard over the Internet network;
    displaying an output of normalized medical data on the dashboard, the dashboard displayed on a user device operably coupled to the Internet, the dashboard configured to:
        enable a user to select one of a set of display options from the set including: a Venn diagram-type output, a scatter plot-type output or an orbit plot-type output;
        display medical data for the patient population captured by the at least one quality measure using the display option selected by the user; and
        enable the user to further interactively select details of a particular data section displayed in the display option.

2. The computer-implemented method of claim 1, wherein when the display option is the Venn-diagram type output, the dashboard is further configured to display medical data by:
    querying the database to obtain all patients in selected panels and populations;
    packaging patient data to transmit to the dashboard;
    displaying a list of populations on the dashboard;
    selecting populations and graphically displaying the union of populations and non-union of populations with other chosen populations;
    selecting patient criteria via intersections or excluded areas;
    querying the database to obtain and return the list of patients meeting the criteria; and
    displaying the patient list meeting the criteria.

3. The computer-implemented method of claim 2, wherein when the display option is the Venn diagram-type output, the dashboard is further configured to display medical data by:
    receiving a user input of an element of the Venn diagram-type output in a user interaction with the Venn diagram-type output;
    retrieving details associated with the desired element; and
    displaying the retrieved details adjacent the element.

4. The computer-implemented method of claim 3, wherein the user interaction is at least one of, clicking, dragging, or hovering over a desired union or non-union population.

5. The computer-implemented method of claim 1, wherein when the display option is the scatter plot-type output, the dashboard is further configured to display medical data by:
    querying the database to obtain a panel of patients and patient demographic and clinical observation data;
    packaging patient data to transmit to the dashboard;
    displaying an individual point on the dashboard, each point designating a patient according to the selected categorical characteristic and continuous characteristics for each patient;
    displaying categorical characteristics via color or shape on the dashboard;
    displaying continuous data on x and y axes via the position of the individual point;
    selecting a subset of patients from the continuous data;
    displaying the number of patients in the subset;
    querying the database to obtain and return the list of patients in the subset; and
    displaying the list of patients in the subset.

6. The computer-implemented method of claim 5, wherein when the display option is the scatter plot-type output, the dashboard is further configured to display medical data by:
  receiving a user input of an element of the scatter plot-type output in a user interaction with the scatter plot-type output;
  retrieving details associated with the individual point; and
  displaying the retrieved details adjacent the element.

7. The computer-implemented method of claim 6, wherein the user interaction is at least one of, clicking, dragging, or hovering over the individual point.

8. The computer-implemented method of claim 1, wherein when the display option is the orbit plot-type output, the dashboard is further configured to display medical data by:
  receiving a selection of the patient;
  querying the database to obtain patient event information based on the selection;
  displaying a circle on the dashboard, the circle depicting the patient;
  selecting a time frame to view via two sliders on a timeline; and
  displaying all patient events and relationships within the selected time frame.

9. A computer-implemented system for the automated visualization of patient medical information and medical data over an Internet network, comprising:
  a processor and non-volatile memory operably coupled to the processor;
  a plurality of datasets, each dataset comprised of medical data of patients for each of at least one medical provider and at least one payor organization, wherein each of the datasets in the plurality of datasets is stored in a computer memory accessible over the Internet network separately from each of the other datasets, each of the plurality of datasets including at least an electronic medical record and a secondary healthcare record, the electronic medical record and the secondary healthcare record stored separately and having at least one common key;
  a normalizer engine stored in the non-volatile memory, executable by the processor and configured to execute database-specific calls to each of the datasets over the Internet network and retrieve at least some of the medical data from the plurality of datasets, the normalizer configured to generate a set of metadata based on the at least one quality measure of the medical data and generate normalized medical data for the set of metadata using a denominator to define a patient population having the at least one quality measure;
  a database populated with the normalized medical data obtained from the normalizer, the database operably coupled to the Internet network, wherein the normalized medical data is stored separately from the plurality of datasets to create a medical data superset for each patient including medical data common to each patient stored among the plurality of datasets;
  an application layer operably coupled to the Internet network and configured to enable communication between the database of the medical data superset for each patient and a dashboard over the Internet network;
  the dashboard configured to display an output of normalized medical data, the dashboard displayed on a user device operably coupled to the Internet, the dashboard configured to:
    enable a user to select one of a set of display options including: a Venn diagram-type output, a scatter plot-type output or an orbit plot-type output;
    display medical data for the patient population captured by at least one quality measure using the display option selected; and
    enable the user to further interactively select details of a particular data section displayed in the display option.

10. The computer-implemented system of claim 9, wherein the selected display option is the Venn diagram-type output, the dashboard is configured to graphically display medical data as overlapping circles wherein the intersections of the circles contain specific patient populations.

11. The computer-implemented system of claim 10, wherein an interaction with the Venn diagram-type output retrieves details associated with the desired population and displays the retrieved details adjacent an element of the Venn diagram-type output.

12. The computer-implemented system of claim 11, wherein the interaction is at least one of, clicking, dragging, or hovering over a desired union or non-union population.

13. The computer-implemented system of claim 9, wherein the selected display option is the scatter plot-type output, the dashboard is configured to graphically display medical data according to categorical characteristics and continuous characteristics of each patient.

14. The computer-implemented system of claim 13, wherein the categorical characteristics and continuous characteristics are displayed in the form of a point, letter, shape, symbol or color.

15. The computer-implemented system of claim 14, wherein an interaction with the characteristics being displayed retrieves details associated with an interacted with characteristic and displays the retrieved details adjacent to the interacted with characteristic.

16. The computer-implemented system of claim 15, wherein the interaction is at least one of, clicking, dragging, or hovering over the interacted with characteristic.

17. The computer-implemented system of claim 9, wherein the selected display option is the orbit plot-type output, the dashboard is configured to display medical data of a particular patient, wherein the patient is graphically depicted as a circle or orbit and patient events are depicted as additional circles or orbits using a selected orbit plot-type output.

18. The computer-implemented system of claim 9, wherein the system is selected from the group consisting of a cloud computing system, client-server system, standalone computer processing environment, and any combination thereof.

19. The computer-implemented system of claim 9, wherein the normalized medical data is a patient data superset.

20. A computer-implemented system for the automated visualization of patient medical information and medical data over an Internet network, comprising:
  means for storing medical data of patients for each of at least one medical provider and at least one payor organization in a plurality of datasets, wherein each of the datasets in the plurality of datasets is stored in a computer memory accessible over the Internet network separately from each of the other datasets, each of the plurality of datasets including at least an electronic medical record and a secondary healthcare record, the electronic medical record and the secondary healthcare record stored separately and having at least one common key;

means for normalizing the medical data by executing database-specific calls to each of the datasets over the Internet network and retrieving at least some of the medical data from the plurality of datasets by a normalizer, the normalizer configured to generate a set of metadata based on at least one quality measure of the medical data and generate normalized medical data for the set of metadata using a denominator to define a patient population having the at least one quality measure;

means for populating a database with the normalized medical data, the database operably coupled to the Internet network, wherein the normalized medical data is stored separately from the plurality of datasets to create a medical data superset for each patient including medical data common to each patient stored among the plurality of datasets;

means for configuring an application layer operably coupled to the Internet network to enable communication between the database of the medical data superset for each patient and a dashboard over the Internet network;

means for displaying an output of normalized medical data on the dashboard, the dashboard displayed on a user device operably coupled to the Internet, the dashboard configured to:
- enable a user to select one of a set of display options from the set including: a Venn diagram-type output, a scatter plot-type output or an orbit plot-type output;
- display medical data for the patient population captured by the at least one quality measure using the display option selected by the user; and
- enable the user to further interactively select details of a particular data section displayed in the display option.

* * * * *